(12) United States Patent
Cuddeback

(10) Patent No.: US 10,477,866 B1
(45) Date of Patent: Nov. 19, 2019

(54) GOOSE AND COOT REPELLENT AND METHOD FOR REPELLING GEESE, COOTS AND OTHER BIRDS

(71) Applicant: David A Cuddeback, 1743 Route 11, NY (US)

(72) Inventor: David A Cuddeback, 1743 Route 11, NY (US)

( * ) Notice: Subject to any disclaimer, the term of this patent is extended or adjusted under 35 U.S.C. 154(b) by 18 days.

(21) Appl. No.: 15/665,916

(22) Filed: Aug. 1, 2017

Related U.S. Application Data

(60) Provisional application No. 62/369,261, filed on Aug. 1, 2016.

(51) Int. Cl.
| | |
|---|---|
| *A61K 36/00* | (2006.01) |
| *A01N 65/20* | (2009.01) |
| *A01N 65/00* | (2009.01) |
| *A01N 65/22* | (2009.01) |
| *A01N 65/08* | (2009.01) |
| *A01N 65/18* | (2009.01) |
| *A01N 63/00* | (2006.01) |
| *A01N 65/42* | (2009.01) |
| *A01N 65/24* | (2009.01) |

(52) U.S. Cl.
CPC ............. *A01N 65/20* (2013.01); *A01N 63/00* (2013.01); *A01N 65/00* (2013.01); *A01N 65/08* (2013.01); *A01N 65/18* (2013.01); *A01N 65/22* (2013.01); *A01N 65/24* (2013.01); *A01N 65/42* (2013.01)

(58) Field of Classification Search
None
See application file for complete search history.

(56) References Cited

U.S. PATENT DOCUMENTS

| | | | | |
|---|---|---|---|---|
| 2007/0181455 | A1* | 8/2007 | Davis ........................ | A61L 2/23 206/362.3 |
| 2015/0216182 | A1* | 8/2015 | Brown ................... | A01N 57/16 424/405 |

* cited by examiner

*Primary Examiner* — Qiuwen Mi
(74) *Attorney, Agent, or Firm* — Malin Haley DiMaggio & Bowen, P.A.

(57) ABSTRACT

A composition, for repelling geese, coots and other ground feeding birds which feed on seeds, grasses, grains, sedges and forbs from a desired area that receives the composition that includes a mixture of peanut hulls as a granular base, cedar oil, thyme oil, cinnamon oil, castor oil, fish oil, garlic oil, and white pepper.

1 Claim, No Drawings

US 10,477,866 B1

GOOSE AND COOT REPELLENT AND METHOD FOR REPELLING GEESE, COOTS AND OTHER BIRDS

CROSS REFERENCE TO RELATED APPLICATIONS

This application claims benefit of U.S. Patent Provisional Application Ser. No. 62/369,261 filed on Aug. 1, 2016.

BACKGROUND OF THE INVENTION

1. Field of the Invention

The composition is a non-water soluble, solid repellent that is particularly useful in repelling geese from lawns, golf courses, athletic fields, corporate campuses, parks, gardens, fields, beaches and other outdoor areas. The composition has also proven to be effective with coots. Its principal composition and related variations indicate effectiveness with crows, starlings, sparrows and all other ground feeding birds which feed on seeds, grasses, grains, sedges and forbs.

The composition is a water based emulsion forming a repellent that is useful in repelling geese, coots, and other birds. In other embodiments, the composition is a suspension of ingredients within water, vegetable or other plant oils or other similar and/or suitable liquid, forming a repellent that is useful in repelling geese, coots, and other birds. And yet in still other embodiments, the composition is a gel containing one or a mix of gelatin, polymers and/or any similar flexible and/or viscous material together with other ingredients forming a repellent that is useful in repelling geese, coots, and other birds.

2. Description of Related Art

Geese often cause extensive damage to golf courses, athletic fields, lawns, gardens, parks, corporate campuses, beaches and municipal areas from geese droppings. For example, the geese population has exploded in many rural and suburban communities, and, as a result, the geese are forced by competition to venture into neighborhoods, parks, lawns and gardens to seek food. Geese consume grasses, particularly newly sprouting blades, and seeds, grains and grain sprouts and other agricultural and decorative sprouts, and bugs living in grasses while also depositing large amounts of droppings anywhere. Coots are aquatic birds that require water to take off and land, and prefer shorelines adjacent to open or grassy land. Coots feed on grass in addition to aquatic vegetation. Since they live in flocks, coots can cause significant damage to parks, golf course fairways, rough and even greens. Coots can also leave behind a massive amount of fecal droppings that collect on park spaces, golf balls, shoes and mowers.

Compositions have been developed to repel geese through repugnant smells and tastes. No other birds referenced above are known to be effectively repelled by these compositions. Many of these repellent compositions are applied directly to the vegetation to be protected. The majority of these repellents simulate the smell or taste of noxious vegetation or a taste that is extremely unpleasant to the geese. These types of repellents are only partially effective in that all employ ingredients which are either subject to rapid deterioration due to rainfall and both sunlight and atmospheric evaporation and degradation or they have been demonstrated to be minimally effective. The most generally known goose repellent consists of a solution of methyl anthranilate—an extract of Concord grape skins. This substance is water soluble and subject to rapid environmental degradation. While it is somewhat effective, it very quickly dissipates when exposed to air and is extremely short lived.

The geese are repelled only from the vegetation on which the repellent is applied, i.e., the geese will continue to invade the lawn, garden, or field of crops and will only avoid those particular plants to which the repellent is topically applied.

Repelling geese and other birds from vegetation and open spaces regularly used by people is an ongoing, perpetual task. Most current repellent compositions are water-soluble, and therefore, must be replaced when dissolved and washed away by precipitation, or where open public spaces or lawns have been mowed. Olfactory repellents must evaporate to produce their desired effect; however, many current olfactory repellents evaporate quickly, thereby losing their repellent effects, and must be replaced often. The need for frequent replacement of the repellent used increases costs for the user. Residential, corporate and municipal property owners, golf courses, farmers, and gardeners have an existing need for a repellent that is non-water soluble and that evaporates slowly over time to prolong the effectiveness of the repellent.

SUMMARY OF THE INVENTION

A goose, coot and bird repellent composition, and more specifically, a composition for repelling one or more geese, coots or other birds away from an area in which vegetation is located or other area that the user desires to protect from geese or coot droppings or seed and vegetation damage. The composition comprises a mixture of peanut hulls as a granular carrier, and oils including cedar oil, thyme oil, cinnamon oil, castor oil, fish oil, and garlic oil. The composition also includes white pepper. The composition is not soluble in water, and thus, is not dissolved and washed away by precipitation. The repellent's insolubility in water produces a longer lasting effect among geese, coots and other birds that the user desires to repel from the protected vegetation or other areas. The amount of each ingredient and the types of oils employed that are used in producing the repellent composition may be varied to prevent desensitization of geese in a protected location to the particular smell or olfactory profile, and taste, of the composition. Varying the amounts of ingredients and types of oils used also allows the product to be adapted for use in repelling several different types and species of geese, coots and other birds. The field lives of the repellent composition are increased by providing variations of the mixture and by the insolubility of the composition in water.

The repellent composition is easily dispensed and applied by the user in an area having vegetation that is to be protected. The repellent composition is also biodegradable and decomposes into useful fertilizer nutrients.

An object of the invention is to provide a composition that is not soluble in water to repel geese, coots, and other birds from golf courses, athletic fields, corporate campuses, lawns, gardens, parks, and other areas in which the user desires to protect vegetation and surfaces from geese and coot droppings and vegetation damage.

Another object of the invention is to provide a method for repelling geese, coots and other birds from golf courses, athletic fields, lawns, gardens, beaches, parks, and other areas in which the user desires to prevent geese and coot droppings and/or damage to vegetation.

DETAILED DESCRIPTION

A composition for repelling geese, coots and other birds using a mixture of ingredients that together and in varying proportions produce an odor and taste, that effectively repel these birds. The composition comprises a solid mixture of peanut hulls as a granular base and oils including cedar oil, thyme oil, cinnamon oil, castor oil, fish oil, and garlic oil.

The composition also includes white pepper. The composition could also be micro encapsulated to improve the time span of effectiveness.

In a preferred embodiment, the composition mixture includes 89.29 percent by weight of peanut hulls, 2.25 percent cedar oil by weight, thyme oil 0.60 percent by weight; cinnamon oil 0.55 percent by weight; castor oil 4.00 percent by weight; fish oil 1.00 percent by weight and garlic oil 0.06 percent by weight. Also composition includes white pepper 2.25% by weight. Each ingredient, several together or all at once may be varied by ranges of up to 50% above or below the percentage by weight stated immediately above. These ranges are used to vary the amount of each ingredient in the repellent mixture to produce several compositions, each composition having a unique olfactory profile or smell or taste. Some variations of the composition may provide better repellent results in certain locales and with certain geese and other birds than in other locales and with different geese or other bird species. The composition is produced and sold as a solid granule or a semi-solid emulsion, suspension or gel.

Because the composition is solid or semi-solid and is not soluble in water, said repellent composition may be scattered or otherwise applied on the ground in and around the location of the vegetation to be protected. Precipitation does not dissolve the repellent composition, and therefore, the effects of the repellent last longer than those of other repellents that are water-soluble. The repellent composition also does not require application directly to the vegetation because a principal repelling characteristic of the composition is olfactory in nature and can create a smell barrier around areas of vegetation needing protection.

Preferably, the repellent composition is produced in mixtures containing different amounts of each ingredient which are periodically interchanged over time to prevent desensitization of geese. The periodic rotation or interchanging of the repellent composition variation used prolongs the effectiveness of said repellent in repelling geese, prevents geese in the user's selected protected location from becoming desensitized or accustomed to the smell, olfactory and/or the taste profile of the composition which does occur with repellents that are unchanging in smell or other characteristics. The core formulation of said repellent composition (described above as the preferred percentage by weight of each ingredient) is varied over time so that the geese that are to be repelled do not lose their fear of the smell of the composition.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A composition for repelling geese comprising:
a mixture of peanut hulls in granular form, cedar oil, thyme oil, cinnamon oil, castor oil, fish oil, garlic oil and white pepper wherein said mixture emits odor that is offensive to repels geese; wherein ingredients of the mixture are included in the following amounts:
89.29 percent by weight peanut hulls;
1.25 percent by weight cedar oil;
0.60 percent by weight thyme oil;
0.55 percent by weight cinnamon oil;
4.0 percent by weight castor oil;
1.0 by weight fish oil;
0.06 by weight garlic oil; and
2.25 by weight white pepper.

* * * * *